United States Patent
Michalske (10) Patent No.: US 10,041,916 B2
(45) Date of Patent: Aug. 7, 2018

(54) METHOD AND DEVICE FOR MONITORING GAS SENSORS

(71) Applicant: Robert Bosch GmbH, Stuttgart (DE)

(72) Inventor: Andreas Michalske, Kornwestheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 605 days.

(21) Appl. No.: 14/386,220

(22) PCT Filed: Jan. 28, 2013

(86) PCT No.: PCT/EP2013/051553
§ 371 (c)(1),
(2) Date: Sep. 18, 2014

(87) PCT Pub. No.: WO2013/139512
PCT Pub. Date: Sep. 26, 2013

(65) Prior Publication Data
US 2015/0047415 A1 Feb. 19, 2015

(30) Foreign Application Priority Data
Mar. 20, 2012 (DE) .......................... 10 2012 204 353

(51) Int. Cl.
*F02D 41/02* (2006.01)
*G01N 33/00* (2006.01)
(Continued)

(52) U.S. Cl.
CPC ..... *G01N 33/0027* (2013.01); *F02D 41/1454* (2013.01); *F02D 41/1458* (2013.01);
(Continued)

(58) Field of Classification Search
USPC ................. 123/443; 701/103, 109
See application file for complete search history.

(56) References Cited

U.S. PATENT DOCUMENTS 7,320,309 B2 * 1/2008 Michalske .......... F02D 41/1405
123/443
9,518,893 B2 12/2016 Michalske
(Continued)

FOREIGN PATENT DOCUMENTS

CN 101069093 A 11/2007
CN 101915737 A 12/2010
(Continued)

*Primary Examiner* — Lam Nguyen
(74) *Attorney, Agent, or Firm* — Norton Rose Fulbright US LLP; Gerard Messina (57) ABSTRACT

A method and a device for monitoring gas sensors in an internal combustion engine, in which in a steady-state operation of the internal combustion engine, the output signal of the gas sensor is filtered by a high-pass filter and higher-frequency signal components are analyzed by a comparison with an appropriately processed model value. When using the method and the device for executing the method, electrically oscillating gas sensors or the incoupling of interference variables or faults in the evaluation circuit, especially in the case of exhaust gas sensors in an exhaust-gas purification and reducing system, are able to be detected, which minimizes faulty interpretations in a dynamic diagnosis. This monitoring function is advantageously combinable with dynamic diagnosis functions that likewise analyze higher-frequency signal components by a comparison with appropriately processed model values. This increases the operational reliability of the exhaust-gas purification or reducing system.

14 Claims, 5 Drawing Sheets

(51) Int. Cl.
    *F02D 41/14*     (2006.01)
    *F02D 41/22*     (2006.01)
    *G01M 15/10*     (2006.01)

(52) U.S. Cl.
    CPC ....... *F02D 41/1495* (2013.01); *F02D 41/222* (2013.01); *G01M 15/102* (2013.01); *G01N 33/0037* (2013.01); *F01N 2560/025* (2013.01); *F02D 2041/1432* (2013.01); *F02D 2041/1433* (2013.01); *Y02A 50/245* (2018.01); *Y02T 10/40* (2013.01)

(56) References Cited

U.S. PATENT DOCUMENTS

2009/0254264 A1* 10/2009 Kirstaetter .......... F02D 41/1454 701/109
2014/0358355 A1   12/2014  Zimmerschied

FOREIGN PATENT DOCUMENTS

| | | |
|---|---|---|
| DE | 10 2008 001121 | 10/2009 |
| DE | 10 2008 040737 | 1/2010 |
| DE | 10 2008 042549 | 4/2010 |
| DE | 10 2009 028367 | 2/2011 |
| EP | 0 810 363 A2 | 12/1997 |
| JP | H05-263626 A | 10/1993 |
| JP | H06-342303 A | 12/1994 |
| JP | H09-096236 A | 4/1997 |
| JP | H10-176578 A | 6/1998 |
| JP | 2003-254138 A | 9/2003 |
| JP | 2004-245604 A | 9/2004 |
| JP | 2006-161695 A | 6/2006 |
| JP | 2008-152318 A | 7/2008 |
| JP | 2009-063329 A | 3/2009 |
| JP | 2010-096015 A | 4/2010 |
| JP | 2011-047319 A | 3/2011 |
| JP | 2011-085061 A | 4/2011 |
| JP | 2015504134 A | 2/2015 |
| JP | 2015511286 A | 4/2015 |

* cited by examiner

METHOD AND DEVICE FOR MONITORING GAS SENSORS

FIELD OF THE INVENTION

The present invention relates to a method for monitoring gas sensors of an internal combustion engine, the gas sensors exhibiting a low-pass behavior as a function of the geometry, measuring principle, aging or contamination; a comparison of a modeled and a measured signal for a diagnosis is performed on the gas state variable to be measured, the measured signal being an actual value of an output signal of the gas sensor, and the modeled signal being a model value. The present invention furthermore relates to a device for implementing the method.

BACKGROUND INFORMATION

To reduce emissions in passenger vehicles equipped with Otto engines, 3-way catalytic converters, which convert exhaust gas to a sufficient degree only if the λ air-fuel ratio is adjusted with high precision, are routinely used as exhaust gas purification systems. For this purpose, the λ air-fuel ratio is measured with the aid of an exhaust-gas sensor situated upstream from the exhaust-gas purification system. The oxygen storage capacity of such an exhaust-gas purification system is utilized for receiving oxygen in lean phases and for releasing it again in rich phases. This allows a conversion of oxidizable pollutant gas components of the exhaust gas. An exhaust-gas sensor postconnected to the exhaust gas purification system monitors the oxygen storage capacity of the exhaust gas purification system. The oxygen storage capacity must be monitored within the framework of the on-board diagnosis (OBD), since it represents a measure of the conversion ability of the exhaust gas purification system.

To determine the oxygen storage capability, either oxygen is applied to the exhaust gas purification system in a lean phase and then discharged in a rich phase having a known lambda value of the exhaust gas, taking the passing exhaust gas quantity into account, or the oxygen in the exhaust gas purification system is first evacuated in a rich phase and then replenished in a lean phase having a known lambda value of the exhaust gas, taking the passing exhaust gas quantity into account. The lean phase is terminated when the exhaust gas sensor postconnected to the exhaust gas purification system detects that the exhaust gas purification system is no longer able to store the oxygen. In the same way, a rich phase is terminated when the exhaust gas sensor detects the passage of rich exhaust gas. The oxygen storage capacity of the exhaust gas purification system corresponds to the quantity of reducing agents supplied for the evacuation during the rich phase or the oxygen quantity supplied for the replenishment during the lean phase. The precise quantities are calculated from the signal of the upstream exhaust gas sensor and from the exhaust gas mass flow determined from other sensor signals.

If the dynamic response of the upstream exhaust gas sensor diminishes, e.g., as a result of contamination or aging, then the air-fuel ratio is no longer able to be adjusted with the required precision, so that the conversion power of the exhaust gas purification system drops. Furthermore, there may be deviations in the diagnosis of the exhaust gas purification system, which may cause an actually properly functioning exhaust gas purification system to be erroneously classified as non-functional. The law requires a diagnosis of the sensor characteristics during a vehicle operation in order to ensure that the prescribed fuel-air ratio continues to be adjustable with sufficient precision, so that the emissions do not exceed the allowed limit values and the exhaust gas purification system is monitored correctly. The OBdII stipulations require monitoring of lambda sensors and other exhaust gas sensors not only with regard to their electrical functioning, but also with regard to their response behavior, i.e., a worsening of the sensor dynamics, which may manifest itself in a greater time constant and/or dead time, must be detected. Dead times and delay times between a change in the exhaust gas composition and its detection requite an on-board check so as to ascertain whether they are still allowable for the usage functions, i.e., for control, regulation and monitoring functions that utilize the sensor signal. Typically, the dead time from a mixture change to the signal flank and a particular rise time, e.g., from 0% to 63% or from 30% to 60% of the signal travel, are used as characteristic quantities for the dynamic characteristics of exhaust gas sensors. The dead time also includes the gas propagation time from the engine outlet to the sensor, and therefore changes in a manipulation of the sensor installation location, in particular.

In Diesel engines, broadband lambda sensors are used as gas sensors or as gas concentration sensors, and in connection with SCR catalysts, $NO_x$ sensors are used as well. The latter additionally also supply an $O_2$ signal. The $O_2$ signal of the broadband lambda sensor or the $NO_x$ sensor is used not only for operating exhaust gas aftertreatment systems in the Diesel engine, but also for the motor-internal emission reduction. The measured $O_2$ concentration in the exhaust gas or the measured lambda signal is used to dynamically adjust the air-fuel mixture in a precise manner and to thereby minimize the deviations in the untreated emissions. In Diesel engines having a $NO_x$ storage catalyst (NST), a separate broadband lambda sensor is needed upstream and downstream from the catalyst in each case in order to reliably represent the rich operation required for the regeneration. An engine-internal emission reduction and an NSC operation also pose certain minimum requirements on the dynamic characteristics of the $O_2$ sensor. Nowadays, the rise time of the $O_2$ signal is monitored during the transition from load to trailing throttle, i.e., in a rise from a certain percentage below the normal $O_2$ content of air, to 21%. If the sensor signal even fails to reach a certain intermediate value after a maximum time, then this will be interpreted as a dead time error. In Diesel engines having a $NO_x$ storage catalyst (NSC), the response behavior of the lambda sensors upstream and downstream from the catalyst is usually compared as well.

For future vehicle generations or model years, it can be expected that monitoring of the sensor dynamics at a dropping $O_2$ concentration will be required as well. In addition, there will be no more trailing throttle phases in hybrid vehicles in the future and thus no phases featuring a constant $O_2$ concentration of 21%. Initial approaches for these supplementary requirements are the active monitoring in the German publication DE 10 2008 001 121 A1 and the observer-based method in DE 10 2008 040 737 A1.

A method for monitoring dynamic characteristics of a broadband lambda sensor is discussed in DE 10 2008 040 737 A1; here, a measured lambda signal, which corresponds to an oxygen concentration in the exhaust gas of an internal combustion engine, is determined with the aid of the broadband lambda sensor, and an observer, which uses the input variables to generate a modeled lambda signal, is assigned to the internal combustion engine, an estimation error signal being generated on the basis of the difference between the modeled lambda signal and the measured lambda signal, or from the difference between a signal derived from the modeled lambda signal and a signal derived from the measured lambda signal. In this context, it is provided that a measure of the dynamic characteristics of the broadband lambda sensor, characterized by a dead time and a response time, is ascertained from an analysis of the estimation error signal or a variable derived therefrom, and that the measure of the dynamic characteristics is compared with predefined limit values in order to evaluate the extent to which the dynamic characteristics of the broadband lambda sensor suffice for an intended operation of the internal combustion engine.

In addition, a method and a device for the online adaptation of an LSU dynamic model is discussed in DE 10 2008 001 569 A1. More specifically, the document relates to a method and a device for adapting a dynamic model of an exhaust gas sensor, which is part of an exhaust gas tract of an internal combustion engine and used to ascertain a lambda value for controlling an air-fuel composition; in parallel therewith, a simulated lambda value is calculated in a control device or in a diagnostic device of the internal combustion engine, and a user function uses both the simulated and the measured lambda value. A step behavior of the exhaust gas sensor is determined in this context, by analyzing a signal change in an excitation of the system during an ongoing vehicle operation, and the dynamic model of the exhaust gas sensor is adapted on the basis of these results of the dynamic model.

Functions for the dynamic monitoring of broadband lambda sensors are utilized to identify the sensor characteristics. Similar requirements as for $O_2$ signals or $O_2$ sensors exist for other gas concentration signals of exhaust gas sensors, e.g., a $NO_x$ signal. Similarities between the monitoring functions must therefore be assumed.

The method according to DE 10 2008 001 121 A1 relates to active monitoring. It includes an excitation by a test injection, which increases both the fuel consumption and emissions. While the method according to DE 10 2008 040 737 A1 is operating passively, it assumes a so-called observer, whose application is costly. In addition, both methods primarily focus on the detection of more substantial dead time changes.

In an application by the applicant, which is German patent document 10 2011 088 296.0, filed on Dec. 12, 2011, another method and device are described for implementing the method for dynamic monitoring of gas sensors of an internal combustion engine, which, for instance, are disposed as exhaust-gas sensors in the exhaust gas tract of an internal combustion engine as part of an exhaust gas monitoring or reducing system or as gas concentration sensors in an air supply of the internal combustion engine. Depending on the geometry, measuring principle, aging or contamination, the gas sensors exhibit a low pass behavior, and a dynamic diagnosis is performed in response to a change in the gas state variable to be detected based on a comparison of a modeled and a measured signal, the measured signal being an actual value of an output signal of the gas sensor, and the modeled signal being a model value. The output signal of the gas sensor is filtered by a high-pass filter, and higher frequency signal components are analyzed when a change occurs in the gas state variable to be measured, such as also a gas concentration.

A change may occur as a result of an excitation of the internal combustion engine. This method makes it possible to detect and quantify changes with regard to the dynamic response in gas sensors. Gas sensors within the meaning of the present invention are sensors which are able to measure the states of a gas and detect changes therein. The state of the gas may be described by a temperature of the gas, a gas pressure, a mass flow rate of a gas and/or a concentration of a particular gas component, e.g., an oxygen component or a $NO_x$ component. Gas sensors have a typical low pass behavior which depends on the geometry of their configuration, for instance. In addition, such sensors may change their response behavior due to aging or external influences (e.g., due to sooting in Diesel engines).

This dynamic diagnosis method is basically suitable for monitoring or identifying a T63 filter time constant of sensors in the air and exhaust gas system of internal combustion engines. To do so, the functionality compares the signal energies of the sensor signal and a model-based reference signal in the range of higher frequencies. In principle, however, it is possible that a slow but electrically oscillating sensor could erroneously be detected as dynamically properly functioning when using the monitoring principle according to German patent document 10 2011 088 296.0, filed on Dec. 12, 2011. For example, this scenario is conceivable when an exhaust gas sensor is heavily contaminated with carbon particulate, but electromagnetic interference is coupled into the cable harness or the evaluation circuit has an electrical fault (double error).

SUMMARY OF THE INVENTION

Therefore, it is an object of this invention to provide a broadening of the dynamic monitoring for gas sensors, which additionally allows a detection of oscillations or a detection of electric interference variables.

It is furthermore an object of the present invention to provide a corresponding device for executing the method.

The objective of the present method is achieved in that in a steady-state operation of the internal combustion engine, the output signal of the gas sensor is able to be filtered by a high-pass filter and higher-frequency signal components are analyzable by a comparison with the appropriately processed model value. For example, the occurrence of relatively high signal energies after the high-pass filtering during a steady-state operation may indicate a fault or an incoupling of interference variables, if the likewise high-pass-filtered signal energies for the model value simultaneously assume relatively low values for the model value during this steady-state operation. Using the method, it is therefore possible to detect electrically oscillating gas sensors or the incoupling of interference variables or faults in the evaluation circuit, which minimizes faulty interpretations in a dynamic diagnosis.

A steady-state detection is required in order to distinguish between noise, interference and useful signals. If a rate of change is detected in the gas state variables to be measured, then a steady-state operation of the internal combustion engine is detectable because a steady-state operation features only slight to virtually no rates of change for the gas state variable to be measured. A model of the physical variable to be measured and a further high-pass filter may be used for this purpose. The state of the gas may be described by a temperature of the gas, a gas pressure, a mass flow rate of a gas and/or a concentration of a particular gas component, e.g., an oxygen component or a $NO_x$ component. In case of an $O_2$ sensor, for example, it is sufficient to convert an air and fuel mass into an $O_2$ concentration and to delay it using a low-pass filter which corresponds to a functional exhaust-gas sensor. This low-pass filter is then to be connected in series with the same high-pass filter as the real exhaust gas sensor. By comparing the two high-pass outputs in steady-state phases, it is possible to infer an oscillating sensor, i.e., an electrical fault.

One method variant provides that the energy or the power of the higher-frequency signal components of the gas sensor and of correspondingly high-pass filtered output signals from a model of the gas sensor be compared to threshold values for the energy or the power, and the presence of electrical faults of the gas sensor or the occurrence of vibrations be inferred based on the comparison.

When an upper threshold value for the energy or the power of the higher-frequency signal components of the gas sensor is exceeded and simultaneously a drop occurs below a lower threshold value for the energy or power of the higher-frequency components of the modeled signal that are determined from the model, an electrically oscillating gas sensor will be inferred. When analyzing the high-pass filtered signal energies $\Phi_S$ for the gas sensor and $\Phi_M$ for the modeled signal, the following applies analogously: If energy $\Phi_M$ of the model path is lower than a lower threshold $\Phi_{unten}$ and energy $\Phi_S$ of the sensor path is simultaneously greater than an upper threshold $\Phi_{oben}$, then this can be interpreted to mean that the engine operating point is approximately constant and the sensor signal fluctuates heavily nonetheless. An oscillating sensor may be inferred in such a case.

In this context it is advantageous if a model time constant $T_M$ stored in the model corresponds to that of a nominal gas sensor and/or if this model time constant as well as the threshold values are adapted as a function of the gas state variables. The parameters for the dynamic performance of a gas sensor, such as an exhaust gas sensor, usually depend on the exhaust gas mass flow, exhaust gas volumetric flow or the exhaust gas speed. It is therefore useful to also adjust model time constant $T_M$ and the threshold values as a function of such a state variable of the exhaust gas.

In one method variant, the integration of the higher-frequency signal components of the sensor signal and the modeled signal are event-controlled or, if a steady-state operation of the internal combustion engine is detected, started and controlled as a function of time or event, i.e., ended following a fixed integration period T or upon a detected change in the operating point. In a pure time control, the event may possibly be discarded in an operating point change within integration period T.

In the case of an event control, signal energies $\Phi_S$ for the gas sensor and $\Phi_M$ for the modeled signal heavily depend on the instantaneous integration period $T_{aktuell}$. In one method variant, it is therefore provided that in case of an event control, the threshold values are adapted as a function of an instantaneous integration period $T_{aktuell}$, which deviates from a typical integration period $T_{norm}$. For example, this may be realized in that threshold values $\Phi_{unten}$ and $\Phi_{oben}$ are applied for a typical integration period $T_{norm}$ and are adapted to instantaneous integration period $T_{aktuell}$ according to $$\Phi_{unten,\ aktuell} = \Phi_{unten,\ norm}(T_{aktuell}/T_{norm}) \quad (1a)$$

$$\Phi_{oben,\ aktuell} = \Phi_{oben,\ norm}(T_{aktuell}/T_{norm}) \quad 1b$$

An alternative method variant consists of not comparing signal energies $\Phi_M$ or $\Phi_S$, but of analyzing an average signal power of the higher-frequency signal components of the sensor signal and the modeled signal and of performing the comparison using an applicable power threshold value. The average signal powers therefore result as follows: $P_M=\Phi_M/T$ and $P_S=\Phi_S/T$. In this case, the integration result is to be divided by the particular integration period T. The threshold values are then to be replaced by corresponding power threshold values $P_{unten}$ and $P_{oben}$. This approach has the advantage that there is no need to adapt the threshold values to the actual integration period.

To improve the selectivity of the diagnosis and the signal-to-noise ratio, the signal of the gas sensor and/or of the modeled signal are/is filtered in addition in the high-pass filtering, using filter units or filter functions that exhibit insensitivity or dead zones in their characteristic curve in the region of small input variables, which may additionally include step changes in their characteristic curve. This suppresses small signal amplitudes, in particular, which may occur due to noise. The use of these additional filter units or filter functions in the high-pass filtering is useful not only in the sensor path, but in the model path as well, because the model typically uses other sensor signals, which may likewise carry noise. If the potential electrical faults are known and have lower frequencies than the noise, it is also possible to use a software low-pass filter before the non-linearities in the signal path.

In corresponding variants for these filter units or filter functions, it may be provided that the characteristic curves of these filter units are combined with the functionality of the squaring of the signals for the purpose of calculating the signal power of the higher-frequency signal components, or that the absolute amount of the high-pass signal output is used or also that the absolute amount generation is combined with the insensitivity or dead zone in a characteristic curve of the filter units.

The monitoring method according to the present invention may be used especially advantageously in gas sensors used as gas pressure sensors, gas temperature sensors, gas mass flow sensors or gas concentration sensors, as exhaust-gas sensors in the exhaust duct of the internal combustion engine as part of an exhaust gas monitoring and reducing system, or in an air supply of the internal combustion engine, e.g., in the suction manifold, in order to detect gas state variables or concentrations. Because of the requirements mentioned in the introduction, these emission-relevant gas sensors must be monitored with regard to their dynamic response and general functioning. A detection of impermissible oscillations is very important for a correct diagnosis result. For example, the response behavior of a gas pressure sensor may be monitored and a diminished dynamic response be detected when the connection of the gas pressure sensor to an intake manifold is clogged or bent, for instance. Gas temperature sensors or gas mass flow sensors may be developed as hot-film air-mass meters within an air supply of the internal combustion engine, for example, in which a dynamics loss may be encountered due to contamination.

When using the method of the present invention, the incoupling of interference signals, which may lead to oscillations, for instance, is able to be detected. To the extent that a suitable model for the signals of such sensors can be provided, the method of the present invention, as described previously in its method variants, may be used to advantage.

In particular exhaust gas sensors in the form of broadband lambda sensors (LSU sensors) or $NO_x$ sensors are conceivable as gas sensors, which can be used to determine an oxygen concentration in a gas mixture. In case of an exhaust gas sensor developed as a broadband lambda sensor or as a continuous exhaust gas sensor, the measured oxygen concentration may be compared to a modeled oxygen concentration for the diagnosis, similar to the previously described method variants. As an alternative, the reciprocal lambda value may be used for this comparison because it is approximately proportional to the oxygen concentration. Also suitable are electrical quantities that are proportional to the oxygen concentration, i.e., a voltage or a current in the sensor or in the associated switching circuit. The model signal utilized for the comparison must then be appropriately converted. For a nitrogen oxide sensor, the output signal of the nitrogen oxide sensor is analyzed as actual value, the model value being determined from a modeled $NO_x$ value. This monitoring can therefore be used to special advantage for Otto engines or for lean engines whose exhaust gas purification system has a catalyst and/or devices for a nitrogen oxide reduction. In these cases, oscillations that occur may have particularly negative consequences for the operation of the exhaust gas purification systems. In gas sensors installed downstream from an exhaust gas purification system, the influence of the exhaust gas purification on the gas concentration in question must be taken into account in the model. As an alternative, it is conceivable to implement the diagnosis only in phases in which the exhaust gas purification does not affect said gas concentration.

Another use of the method with its previously described variants generally may be for processes that use at least one sensor, in which the process is able to be approximated by a first order filter featuring a time constant and possibly a dead time, and in which the behavior of a slowing sensor is able to be described by an increased filter time constant. The previously described advantages with regard to an evaluation of the response behavior of the sensor are basically obtained in this case as well. In addition, such a process can be improved in its control behavior by adapting its controller to the changed time constant.

If, as provided by a method variant, the functionality of the afore-described monitoring method is combined with methods for a dynamic diagnosis of gas sensors, in which, for a diagnosis, an evaluation of higher-frequency signal components is implemented in response to a change of the gas state variable to be measured, the robustness of the dynamic diagnosis method is able to be increased considerably, because the faulty interpretations caused by the incoupling of interference signals, as mentioned in the introduction, are able to be avoided for the most part. The additional application expense is relatively low in such a case, because all of the essential function elements to which the monitoring function has access are already provided by the dynamic diagnosis. The dynamics diagnosis may be performed in operating phases that exhibit changes in the gas state variable to be measured, and monitoring with regard to oscillations of the system or potential electrical faults are able to take place in steady-state phases. German patent document 10 2011 088 296.0, filed on Dec. 12, 2011 in the introduction offers itself as one potential diagnosis method.

The object relating to the device is achieved by providing a monitoring unit for executing the method of the present invention, which includes high-pass filters for analyzing higher-frequency signal components, and at least one model for the gas sensor and calculation units as well as additional filter units or filter functions for executing the monitoring according to the previously described method with its variants. The monitoring unit may be an integral part of the superposed engine control. The functionality of the method may thereby be implemented in an at least partially software-based manner.

In the following text the present invention will be explained in greater detail with reference to an exemplary embodiment shown in the figures.

DETAILED DESCRIPTION

Figure 1:
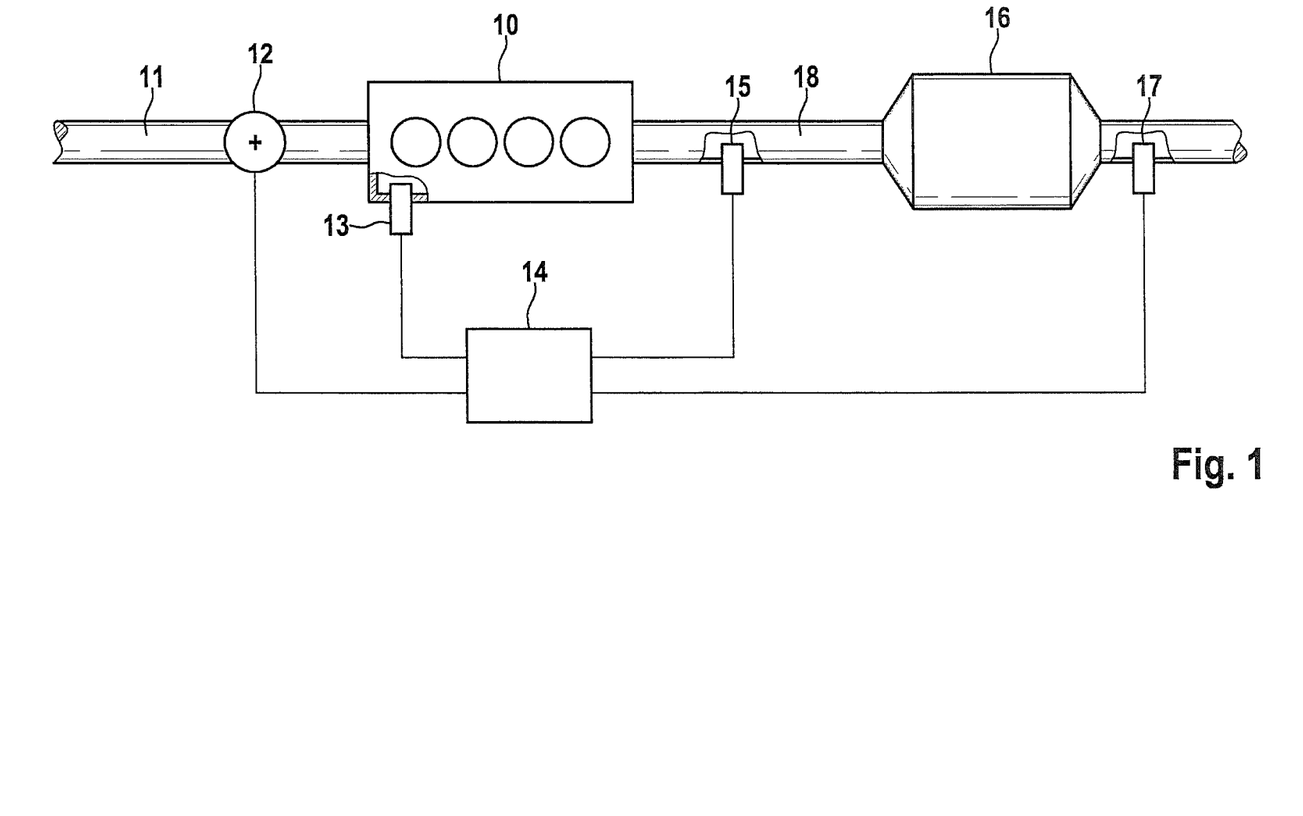
FIG. 1 shows in a schematic representation, the technical environment in which the method according to the present invention is able to be used.

Using an Otto engine as example, FIG. 1 schematically shows the technical environment in which the method for diagnosing an exhaust gas sensor 15 according to the invention is able to be used. An internal combustion engine 10 is supplied with air via an air supply 11, its mass being determined by an air mass meter 12. Air mass meter 12 may be configured as a hot-film air-mass meter, for example. The exhaust gas of internal combustion engine 10 is discharged via an exhaust gas duct 18, and an exhaust gas purification system 16 is provided downstream from internal combustion engine 10 in the flow direction of the exhaust gas. Exhaust gas purification system 16 usually includes at least one catalyst.

An engine controller 14 is provided for the control of internal combustion engine 10, which first of all, supplies fuel to internal combustion engine 10 via a fuel metering device 13 and, secondly, receives the signals of air mass meter 12 and exhaust gas sensor 15 disposed in exhaust duct 18 and an exhaust gas sensor 17 situated in exhaust discharge line 18. In the example illustrated, exhaust gas sensor 15 determines an actual lambda value of a fuel-air mixture supplied to internal combustion engine 10. It may be developed as a broadband lambda sensor or as a continuous lambda sensor. Exhaust gas sensor 17 determines the exhaust gas composition downstream from exhaust gas purification system 16. Exhaust-gas sensor 17 may be developed as a step-change sensor or as a binary sensor.

For better monitoring of the dynamics of exhaust gas sensor 15, it may be provided to use high- and low-pass filters in order to check whether exhaust gas sensor 15 is still able to detect the higher-frequency components of a concentration change in a load change of internal combustion engine 10. Such gas sensors have a characteristic low pass behavior, which depends on the geometry of their protective sleeve, among other things. In Diesel engines, such a protective sleeve may be contaminated with soot, so that the bandwidth of the sensor decreases. In the time range, the decreasing limit frequency manifests itself in a greater rise time, i.e., the signal flanks become flatter in response to the same excitation. If a suitable high-pass filter is therefore connected in series with the sensor, it is possible in steep load changes to detect from the output signal of the high pass whether the limit frequency of the low pass is greater or smaller than the limit frequency of the high pass. The dynamic response of the sensor may be inferred by analyzing these higher-frequency signal energies, as described in German patent document 10 2011 088 296.0, filed on Dec. 12, 2011.

If the signal energy of an exhaust gas sensor 15 assumes an implausibly high value following the high-pass filtering in the steady-state operation, it is furthermore possible to infer an electrical oscillation or an incoupling of interference signals. A model may be used as reference for the plausibility check, as described in German patent document 10 2011 088 296.0, filed on Dec. 12, 2011.

The present invention utilizes a filter system from German patent document 10 2011 088 296.0, filed on Dec. 12, 2011 for searching for high-frequency components in the sensor signal that should actually not be present, during steady-state engine operating phases. If a suitable high-pass filter is connected in series with exhaust gas sensor 15, the steady component and low-frequency components of the measuring signal are suppressed. Only the measuring noise may therefore contribute to the output power of the high-pass filter in a steady-state engine operation.

Figure 2:
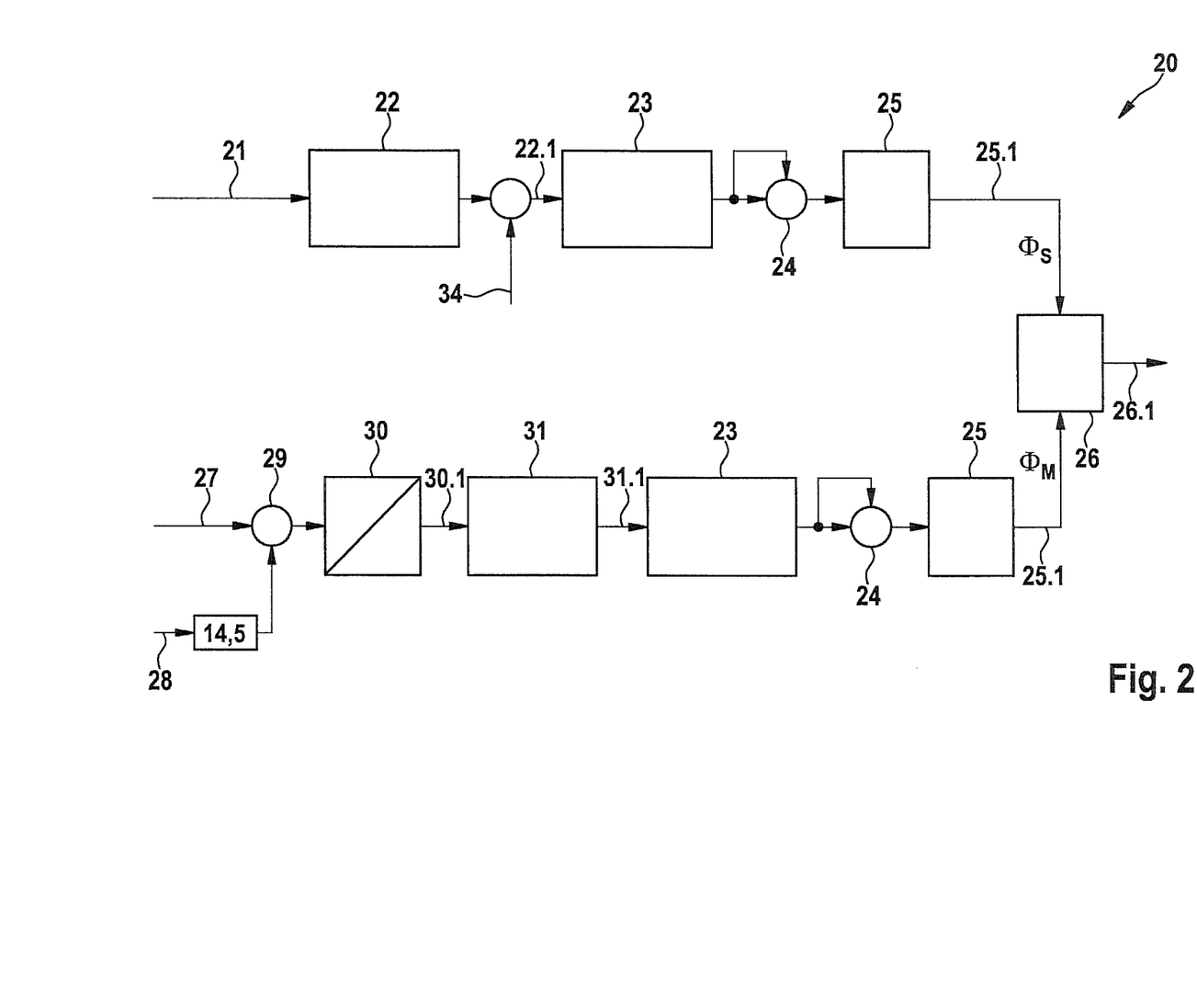
FIG. 2 shows a block diagram of a dynamic diagnosis circuit including a comparison of a signal energy, which can be used as the basis of a plausibility check for detecting oscillations or in coupled electrical interference variables.

FIG. 2 shows the basic structure of the dynamics monitoring from German patent document 10 2011 088 296.0, filed on Dec. 12, 2011 in the form of a block diagram 20. Shown in the upper portion is a path for an oxygen concentration 21 measured using exhaust gas sensor 15. Because of a real gas propagation time and sensor delay 22, which are able to be described by a dead time $T_t$ or a first order low-pass filter having a sensor time constant $T_S$, an oxygen sensor signal 22.1 results on the basis of actual oxygen concentration 21. The transfer function of the sensors and gas propagation time 22 is obtained from the following relationship, in which $K_S$ represents an amplification factor for the sensor:

$$G(j\omega)=K_S \exp(-T_t j\omega)/(T_S j\omega+1) \tag{2}$$

$K_S$ normally corresponds to the multiplicative or rise error of the sensor that stems from production variances and aging. However, if it is not the oxygen concentration that is used as the sensor signal, but a variable that is proportional to said concentration, then $K_S$ is a corresponding transfer coefficient for converting the sensor signal into an oxygen concentration and may also be dimensional. Afterwards, oxygen sensor signal 22.1 is filtered by a high pass 23 and squared using a multiplier 24, thereby obtaining a signal that corresponds to a signal power. An integrator 25 subsequently integrates this signal, so that a signal energy 25.1 of the higher-frequency energy components of the measured oxygen content is obtained. A comparison with a correspondingly conditioned signal for a value ascertained with the aid of a model in a downstream evaluation unit 26 results in a status value 26.1, which may be used for the diagnosis.

Because of incouplings on the cable harness or electrical faults of the evaluation circuit, for example, electrical interference variables 34 may be coupled into the sensor path, as shown in FIG. 2. The low pass behavior of the sensor naturally has no effect on the spectrum of the interference variables. Accordingly, sooting of the sensor, for example, has no effect on the fault sensitivity of the sensor path either.

In the most basic case, high pass 23 may be developed as a first order high pass, whose transfer function is able to be described by the relation $$G(j\omega)=T_F j\omega/(T_F j\omega+1) \tag{3}$$

using $T_F$ as limit frequency of the filter. If the limit frequency of exhaust gas sensor 15 exceeds limit frequency $T_F$ of high pass 23, then the series connection behaves like a band pass, i.e., the high frequencies of the input spectrum of exhaust gas sensor 15 are still permitted to pass and may be detected in the output spectrum. In contrast, if the limit frequency of exhaust gas sensor 15 drops below limit frequency $T_F$ of high pass 23 due to a loss in dynamics, then the series circuit blocks all frequencies, so that it is no longer possible to measure any frequency components at all in the output spectrum.

In principle, the present invention is not restricted to first order high pass filters. Instead, it is also possible to use any other high pass filters. In the same way, the monitoring method is usable when the low pass filters including exhaust gas sensor 15 itself are parameterized in a different manner, e.g., using a limit frequency instead of the time constant, or when they are of a higher order.

To make it possible to distinguish between a slow exhaust gas sensor 15 and insufficient excitation when using the method from German patent document 10 2011 088 296.0, filed on Dec. 12, 2011, the rate of change of the exhaust gas composition must be evaluated, which in the case of a broadband lambda sensor, for example, may be accomplished on the basis of a change in the air and fuel mass. A similar series connection of filters may be used for this purpose. In the case of a broadband lambda sensor, this will require no more than converting the above masses into an $O_2$ concentration and a delay using a low pass filter which corresponds to a functional exhaust gas sensor. This low pass filter must then be switched in series with a high pass that features the same transfer function as the real sensor. By comparing the two high pass outputs, it will then be possible to infer the operativeness of the real sensor. In case of another gas component, it may become necessary to use an additional untreated emissions model.

The processing of the energy value determined with the aid of a model is illustrated in the lower part of block diagram 20 in FIG. 2. Following a stoichiometric correction, a quotient is formed in a division unit 29 from an air mass $27_{mL}$ and a setpoint fuel mass 28 $m_K$ for fuel metering 13, and a lambda value is calculated. Fuel mass 28 may result from the torque request specified by the driver, which is converted into a fuel quantity. In a conversion unit 30, the lambda value is used to determine a calculated oxygen content 30.1. According to a model 31, the transfer function $$G(j\omega)=\exp(-T_{tM} j\omega)/(T_M j\omega+1) \tag{4}$$

is used to calculate a modeled oxygen content 31.1, $T_{tM}$ representing a model dead time, and $T_M$ representing a model time constant.

Modeled oxygen content 31.1 then is filtered by another high pass 23, whose transfer function in the most basic case corresponds to that of the first order high pass, and squared by a further multiplier 24, which results in a signal that corresponds to a signal power. This signal is subsequently integrated by another integrator 25, so that signal energy 25.1 is obtained for the higher-frequency energy components of the modeled oxygen content.

Since high pass 23 suppresses the steady component and the lower-frequency components, only the higher-frequency components of the individual $O_2$ signal 22.1, 31.1 render a contribution. In the steady-state operation, the two high pass output signals $Y_S$ for the sensor signal and $Y_M$ for the model signal should therefore vanish, if the noise is disregarded. The two signal energies 25.1

$$\Phi_M = \int_0^T Y_M^2(t)dt \tag{5a}$$

$$\Phi_S = \int_0^T Y_S^2(t)dt \tag{5b}$$

should consequently likewise assume very low values in the steady-state operation, T representing the integration period.

The comparison of the two signal energies 25.1 in evaluation unit 26 now makes it possible to infer an electrical fault of exhaust gas sensor 15. If energy $\Phi_M$ of the model path is lower than a lower threshold $\Phi_{unten}$, and energy $\Phi_S$ of the sensor path is simultaneously greater than an upper threshold $\Phi_{oben}$, this may be interpreted to mean that the engine operating point is approximately constant and the sensor signal fluctuates nevertheless, which points to an electrically oscillating exhaust gas sensor 15. In summary, the following applies:

$$\Phi_M<\Phi_{unten} \text{ und } \Phi_S>\Phi_{oben} \rightarrow \text{sensor is oscillating}$$

To improve the selectivity of the diagnosis, it is advisable to use a so-called insensitivity or dead zone, as is common practice when filtering noise. This suppresses small values of its input variable in an applicable range. This insensitivity zone may be realized by additional filter units 32, 33 shown in FIGS. 3a, 3b, 4a, 4b as well as 5a and 5b or by filter functions with their characteristic curves, for example, which may also feature a step change (filter unit 33 in each case).

Figure 3A:
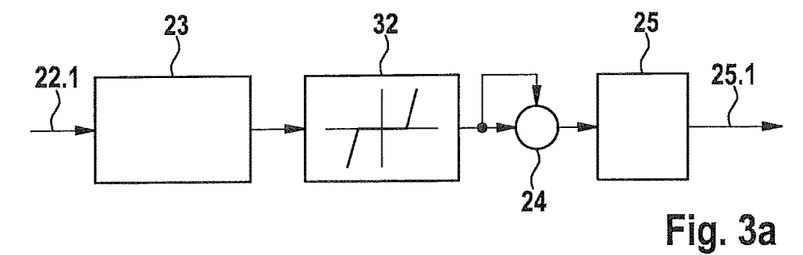
FIGS. 3a and 3b show a high-pass filter as part of the dynamic diagnosis circuit including a filter unit which has an insensitivity region without (FIG. 3a) and with a step change (FIG. 3b).

FIG. 3a shows the sensor path in a cutaway view. Oxygen sensor signal 22.1 is filtered by high pass 23, which has a filter unit featuring an insensitivity region (dead zone) without step change 32. The signal filtered in this manner is then squared by multiplier 24 and integrated using integrator 25, so that signal energy 25.1 is obtained on the output side.

Small signal amplitudes about the zero point are suppressed in this case, as is obvious from the characteristic curve.

Figure 3B:
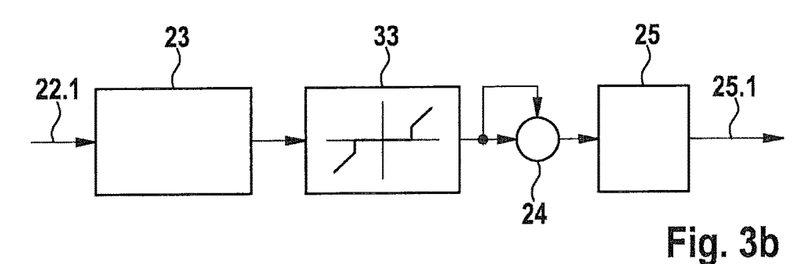

FIG. 3b shows a system as an alternative to that of FIG. 3a; here, a filter unit 33 having an insensitivity region with a step change is used, which also increases the selectivity.

The insensitivity or dead zone may be combined with the squaring in a characteristic curve. In the same way, it is possible to use the absolute amount of the high pass output signal, and it is also possible to combine the absolute value generation with the dead zone in a characteristic curve. These variants are shown in FIGS. 4a, 4b as well as 5a and 5b.

Figure 4A:
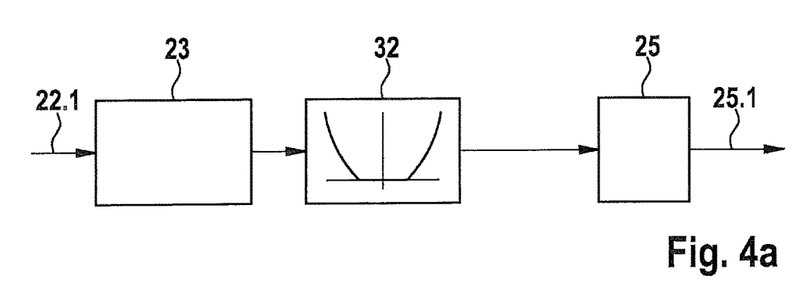
FIGS. 4a and 4b show two alternative developments of the insensitivity region without a step change.

FIG. 4a shows a filter unit 32 having an insensitivity region (dead zone) without step change, in which the characteristic curve is configured as a parabola, so that multiplier 24 may be omitted since the parabola-shaped transfer function of filter unit 32 already generates a squared signal on the output side.

Figure 4B:
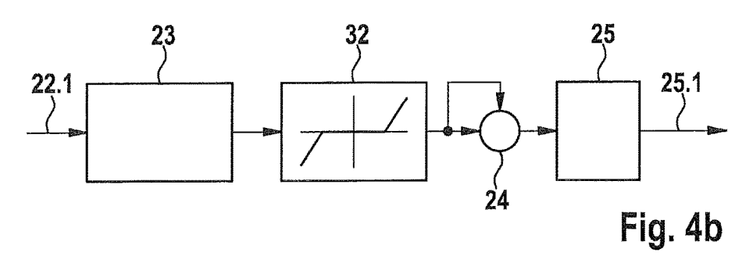

FIG. 4b shows a filter unit 32 having an insensitivity region (dead zone) without a step change, in which the absolute-value generation is combined with the dead zone in a characteristic curve.

Figure 5A:
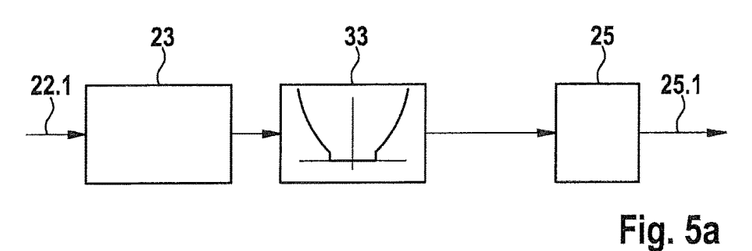
FIGS. 5a and 5b show two alternative developments of the insensitivity region with a step change.
Figure 5B:
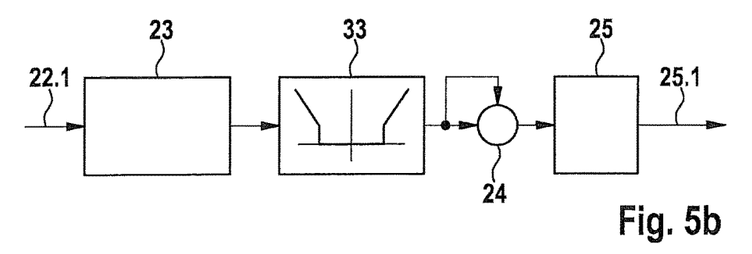

FIGS. 5a and 5b show systems as alternatives to those of FIGS. 4a and 4b, in which the characteristic curve of filter unit 33 features a step change in the insensitivity region.

Figure 6:
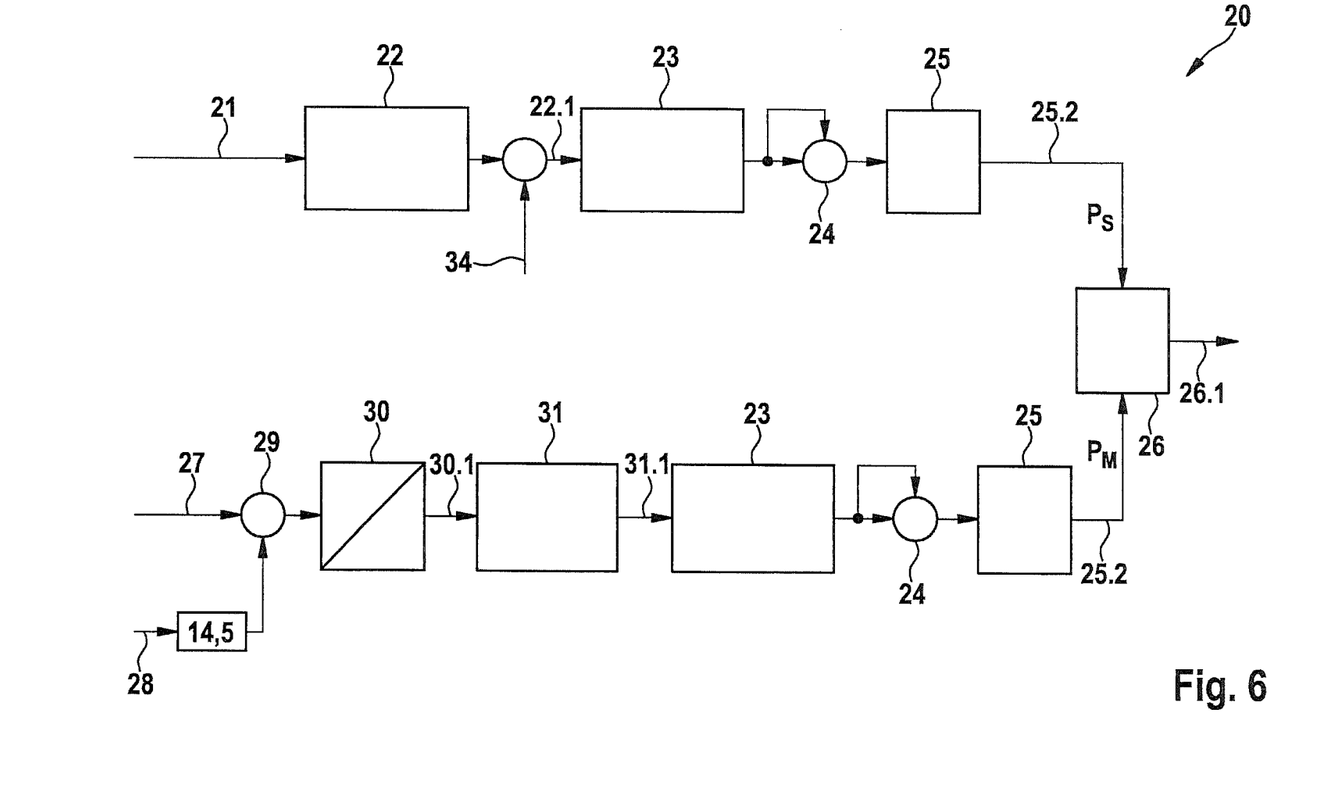
FIG. 6 show a block diagram of a dynamic diagnosis circuit, as an alternative to the one in FIG. 2, featuring a comparison of an average signal power.

FIG. 6 shows a corresponding system, in which, in a deviation from the system shown in FIG. 2, integrator 25 divides the result by integration period T in each case, which means that the average signal powers 25.2 for $P_S$ and $P_M$ are available for the comparison. The comparison then takes place as follows:

$$\Phi_M<\Phi_{unten} \text{ und } \Phi_S>\Phi_{oben} \rightarrow \text{sensor is oscillating}$$

Such a power comparison is of course combinable with all previously mentioned insensitivity regions according to FIGS. 3a, 3b, 4a, 4b as well as 5a and 5b.

The use is conceivable both in gasoline or diesel combustion engines that require an oscillation detection of gas sensors, as may be the case in particular in sensors that are relevant for the exhaust gas. This monitoring function may be used as an autonomous function or combined with dynamic diagnosis functions, e.g., as described in German patent document 10 2011 088 296.0, filed on Dec. 12, 2011.

What is claimed is:

1. A method for diagnosing a gas sensor of an internal combustion engine, the method comprising:
   comparing a modeled signal and a measured signal of a gas state variable to provide a comparison thereof;
   performing a dynamic diagnosis in response to a change in the gas state variable based on the comparison of the modeled signal and the measured signal, the measured signal being an actual value of an output signal of the gas sensor, and the modeled signal being a model value based on input variables of the internal combustion engine, wherein in a steady-state operation of the internal combustion engine, the output signal of the gas sensor is filtered by a high-pass filter, wherein the dynamic diagnosis includes analyzing a signal energy of higher-frequency signal components of the measured signal by comparing the signal energy with a signal energy of a processed model value;
   wherein the gas sensor exhibits a low-pass behavior as a function of a geometry of a protective sleeve, a measuring principle, an aging or a contamination, wherein the high-pass filter is connected in series with the gas sensor, which exhibits a low-pass behavior, and for steep load changes, an output signal of the high-pass filter is used to detect whether a limit frequency of the low-pass behavior of the gas sensor is greater or smaller than another limit frequency of the high-pass filter, and
   wherein the dynamic diagnosis includes inferring an electrical fault of the gas sensor or an occurrence of a vibration based on the comparison.

2. The method of claim 1, wherein a rate of change of the gas state variables to be measured is ascertained and is used to detect a steady-state operation of the internal combustion engine.

3. The method of claim 1, wherein the energy or the power of the higher-frequency signal components of the gas sensor and of correspondingly high-pass filtered output signals from a model of the gas sensor is compared to threshold values for the energy or the power, and the presence of electrical faults of the gas sensor or the occurrence of oscillations is inferred based on the comparison.

4. The method of claim 3, wherein when an upper threshold value for the energy or the power of the higher-frequency signal components of the gas sensor is exceeded, and a simultaneous drop occurs below a lower threshold value for the energy or the power of the higher-frequency signal components of the modeled signal determined from the model, an electrically oscillating gas sensor is inferred.

5. The method of claim 1, wherein a model time constant stored in the model corresponds to that of a nominal gas sensor and/or this model time constant as well as the threshold values are adapted as a function of the gas state variables.

6. The method of claim 1, wherein the integration of the higher-frequency signal components of the sensor signal and the modeled signal is event-controlled or, if a steady-state operation of the internal combustion engine is detected, is started and terminated in a time-controlled or event-controlled manner.

7. The method of claim 6, wherein in case of an event control, the threshold values are adapted as a function of an instantaneous integration period, which deviates from a typical integration period.

8. The method of claim 1, wherein an average signal power of the higher-frequency signal components of the sensor signal and the modeled signal is analyzed, and the comparison takes place with an applicable power threshold value.

9. The method of claim 1, wherein in the high-pass filtering the signal of the gas sensor and/or of the modeled signal is additionally filtered using filter units or filter functions that exhibit insensitivity or dead zones in their characteristic curve in the range of small input variables, which may feature step changes in their characteristic curve in addition.

10. The method of claim 9, wherein the characteristic curves of these filter units or filter functions are combined with the functionality of squaring the signals, or the absolute amount of the high-pass signal output is used or the absolute value generation is combined with the insensitivity or dead zone in one characteristic curve of the filter units.

11. The method of claim 1, wherein, as gas sensors, gas pressure sensors, gas temperature sensors, gas mass flow sensors or gas concentration sensors are used as exhaust gas sensors in the exhaust duct of the internal combustion engine, as part of an exhaust-gas monitoring and reducing system, or in an air supply of the internal combustion engine.

12. The method of claim 1, wherein exhaust gas sensors in the form of broadband lambda sensors or $NO_x$ sensors are used as gas sensors to ascertain an oxygen concentration in a gas mixture.

13. The method of claim 1, further comprising:
using a process for dynamically diagnosing gas sensors, in which an analysis of higher-frequency signal components in a change of the gas state variable to be measured is performed for the dynamic diagnosis.

14. A device for diagnosing a gas sensor in the exhaust duct of an internal combustion engine as part of an exhaust gas monitoring and reducing system or in an air supply of the internal combustion engine, comprising:
a diagnosing arrangement, in a monitoring unit, to perform a diagnosis in response to a change in a gas state variable to be measured, based on a comparison of a modeled signal and a measured signal, the measured signal being an actual value of an output signal of the gas sensor, and the modeled signal being a model value based on input variables of the internal combustion engine, wherein the monitoring unit has high-pass filters for analyzing higher-frequency signal components of the measured signal and at least one model value for the gas sensor, wherein the diagnosing arrangement is configured to analyze a signal energy of higher-frequency signal components by a comparison with a signal energy of an appropriately processed model value;
wherein the gas sensor exhibits a low-pass behavior as a function of a geometry of a protective sleeve, a measuring principle, an aging or a contamination, wherein the high-pass filter is connected in series with the gas sensor, which exhibits a low-pass behavior, and for steep load changes, an output signal of the high-pass filter is used to detect whether a limit frequency of the low-pass behavior of the gas sensor is greater or smaller than another limit frequency of the high-pass filter, and
wherein the diagnosing arrangement infers an electrical fault of the gas sensor or an occurrence of a vibration based on the comparison.

* * * * *